United States Patent
Ueda et al.

(10) Patent No.: US 11,248,282 B2
(45) Date of Patent: Feb. 15, 2022

(54) MAGNESIUM ALLOY

(71) Applicants: FUJI LIGHT METAL CO., LTD., Kumamoto (JP); Japan Medical Device Technology Co., LTD., Kumamoto (JP)

(72) Inventors: Hironori Ueda, Kumamoto (JP); Masashi Inoue, Kumamoto (JP); Makoto Sasaki, Kumamoto (JP)

(73) Assignees: FUJI LIGHT METAL CO., LTD., Kumamoto (JP); Japan Medical Device Technology Co., LTD., Kumamoto (JP)

( * ) Notice: Subject to any disclaimer, the term of this patent is extended or adjusted under 35 U.S.C. 154(b) by 38 days.

(21) Appl. No.: 16/506,298

(22) Filed: Jul. 9, 2019

(65) Prior Publication Data

US 2019/0330718 A1    Oct. 31, 2019

Related U.S. Application Data

(63) Continuation of application No. PCT/JP2017/046768, filed on Dec. 26, 2017.

(30) Foreign Application Priority Data

Jan. 10, 2017  (JP) .............................. JP2017-001887

(51) Int. Cl.
  *C22C 23/04*    (2006.01)
  *A61L 31/02*    (2006.01)

(52) U.S. Cl.
  CPC ............ *C22C 23/04* (2013.01); *A61L 31/022* (2013.01)

(58) Field of Classification Search
  CPC .............................. A61L 31/022; C22C 23/04
  See application file for complete search history.

(56) References Cited

U.S. PATENT DOCUMENTS

| | | | |
|---|---|---|---|
| 5,342,576 | A | 8/1994 | Whitehead |
| 6,080,177 | A | 6/2000 | Igaki et al. |
| 8,569,333 | B2 | 10/2013 | Mollison et al. |
| 9,254,350 | B2 | 2/2016 | Udipi et al. |
| 9,474,637 | B2 | 10/2016 | Zhao |
| 9,480,550 | B2 | 11/2016 | Yamauchi |
| 9,510,932 | B2 | 12/2016 | Kumta et al. |
| 9,522,220 | B2 | 12/2016 | Edick |
| 9,593,397 | B2 | 3/2017 | Imwinkelried et al. |

(Continued)

FOREIGN PATENT DOCUMENTS

| | | |
|---|---|---|
| CN | 1809701 A | 7/2006 |
| CN | 101257860 A | 9/2008 |

(Continued)

OTHER PUBLICATIONS

Xu, Shi-Wei et al., CN-104046867-A: High-plasticity heat-conducting magnesium alloy and preparation method thereof, Sep 17, 2014, CNIPA, translated EPO copy (Year: 2014).*

(Continued)

*Primary Examiner* — Christopher S Kessler
*Assistant Examiner* — Andrew M Cheung
(74) *Attorney, Agent, or Firm* — Kagan Binder, PLLC

(57) ABSTRACT

Magnesium alloy containing, in % by mass, 1.0 to 2.0% of Zn, 0.05 to 0.80% by mass of Zr, 0.05 to 0.40% by mass of Mn, and the balance consisting of Mg and unavoidable impurities. The magnesium alloy may further contain, in % by mass, 0.005% or more and less than 0.20% of Ca.

10 Claims, 2 Drawing Sheets

(56) References Cited

U.S. PATENT DOCUMENTS

| | | | |
|---|---|---|---|
| 10,052,405 B2 | 8/2018 | Koo et al. | |
| 10,350,093 B2 | 7/2019 | Fan et al. | |
| 2002/0004060 A1 | 1/2002 | Heublein et al. | |
| 2005/0033414 A1 | 2/2005 | Zhang et al. | |
| 2005/0043788 A1 | 2/2005 | Luo et al. | |
| 2006/0130947 A1 | 6/2006 | Oishi et al. | |
| 2007/0135908 A1 | 6/2007 | Zhao | |
| 2008/0071358 A1 | 3/2008 | Weber et al. | |
| 2009/0011699 A1 | 1/2009 | Murakami et al. | |
| 2009/0090479 A1 | 4/2009 | Westengen et al. | |
| 2009/0116994 A1 | 5/2009 | Luo et al. | |
| 2009/0131540 A1 | 5/2009 | Hiromoto et al. | |
| 2010/0145436 A1 | 6/2010 | Weber et al. | |
| 2010/0262228 A1 | 10/2010 | Udipi et al. | |
| 2010/0305684 A1 | 12/2010 | Kim et al. | |
| 2013/0004362 A1 | 1/2013 | Soba et al. | |
| 2013/0090741 A1 | 4/2013 | Guo et al. | |
| 2013/0209195 A1 | 8/2013 | Kuwabara et al. | |
| 2014/0200652 A1* | 7/2014 | Bayer | C23F 3/03 623/1.15 |
| 2014/0277396 A1 | 9/2014 | Mendelson et al. | |
| 2015/0196691 A1 | 7/2015 | Covelli et al. | |
| 2016/0022863 A1 | 1/2016 | Decker et al. | |
| 2016/0022876 A1* | 1/2016 | Imwinkelried | A61F 2/44 623/1.15 |
| 2016/0024629 A1 | 1/2016 | Liang et al. | |
| 2016/0129162 A1 | 5/2016 | Pulugurtha et al. | |
| 2018/0264180 A1 | 9/2018 | Sasaki et al. | |
| 2019/0343666 A1 | 11/2019 | Sasaki et al. | |
| 2020/0139017 A1 | 5/2020 | Meyer-Kobbe et al. | |

FOREIGN PATENT DOCUMENTS

| | | | |
|---|---|---|---|
| CN | 101468216 A | | 7/2009 |
| CN | 101629260 A | | 1/2010 |
| CN | 102387825 A | | 3/2012 |
| CN | 102548589 A | | 7/2012 |
| CN | 102719717 A | | 10/2012 |
| CN | 104046867 A | * | 9/2014 |
| CN | 104498790 A | | 4/2015 |
| CN | 104630587 A | * | 5/2015 |
| CN | 104630587 A | | 5/2015 |
| CN | 105143483 A | | 12/2015 |
| CN | 105256213 A | * | 1/2016 |
| CN | 105256213 A | | 1/2016 |
| CN | 105586521 A | | 5/2016 |
| CN | 107385419 A | | 11/2017 |
| EP | 0482947 A1 | | 4/1992 |
| GB | 851871 A | | 10/1960 |
| JP | 35-18704 B1 | | 12/1960 |
| JP | 09256099 A | | 9/1997 |
| JP | 2842943 B2 | | 1/1999 |
| JP | 2004-183062 A | | 7/2004 |
| JP | 2005531391 A | | 10/2005 |
| JP | 2006087704 A | | 4/2006 |
| JP | 2009530039 A | | 8/2009 |
| JP | 2010013725 A | * | 1/2010 .......... C22F 1/06 |
| JP | 2010503486 A | | 2/2010 |
| JP | 2012-082474 A | | 4/2012 |
| JP | 2013215332 A | | 10/2013 |
| JP | 5425364 B2 | | 2/2014 |
| JP | 2014534841 A | | 12/2014 |
| JP | 5701497 B2 | | 4/2015 |
| JP | 2017501756 A | | 1/2017 |
| WO | 2007108450 A1 | | 9/2007 |
| WO | 2007112006 A2 | | 10/2007 |
| WO | 2008036554 A2 | | 3/2008 |
| WO | 2010117537 A2 | | 10/2010 |
| WO | 2013052791 A2 | | 4/2013 |
| WO | 2013052856 A2 | | 4/2013 |
| WO | 2015147184 A1 | | 10/2015 |
| WO | 2018122418 A1 | | 7/2018 |
| WO | 2018139647 A1 | | 8/2018 |

OTHER PUBLICATIONS

Agarwal, Sankalp et al., Biodegradable magnesium alloys for orthopaedic applications: A review on corrosion, biocompatibility and surface modifications, Nov. 1, 2016, Materials Science and Engineering: C, vol. 68, pp. 948-963 (Year: 2016).*
Chino, Yasumasa et al., JP-2010013725-A: Easily formable magnesium alloy sheet and method for production thereof, Jan. 21, 2010, JPO, translated EPO copy (Year: 2010).*
International Preliminary Report on Patentability and English Translation thereof for International Application No. PCT/JP2017/046768, dated Jul. 25, 2019 (8 pages).
International Search Report and English Translation thereof for International Application No. PCT/JP2017/046768, dated Oct. 4, 2018 (2 pages).
English Abstract for WO2007108450A1.
English Abstract for JP2004-183062A.
English Abstract for JP2012-082474A.
Extended European Search Report for European Application No. 17891541.9, dated May 6, 2020 (8 pages).
Database Compendex (Online), "Microstructure and properties of Mg—3Zn—0.8Zr—xMn alloy", Database accession No. E20151300692382, Engineering Information, Inc., New York, NY, US, vol. 36, No. 2, pp. 27-31, Feb. 25, 2015, (1 page).
Gui et al., "Mechanical and corrosion properties of Mg—Gd Zn—Zr—Mn biodegradable alloy by hot extrusion", Journal of Alloys and Compounds, Elsevier Sequoia, Lausanne, CH, vol. 685, pp. 222-230, May 24, 2016, (9 pages).
First Chinese Office Action and English Translation thereof for Chinese Application No. 201780082913.4, dated Oct. 20, 2020 (13 pages).
English Abstract for CN101629260A.
English Abstract for CN104630587A.
English Abstract for CN105256213A.
Yamamoto, "Biomedical Application of Magnesium Alloys," Journal of Japan Institute of Light Metals, vol. 58, No. 11, pp. 570-576, 2008, (13 pages).
Maeda et al., "Fabrication and mechanical properties of biodegradable magnesium stent," Journal of Japan Institute of Light Metals, vol. 66, No. 6, pp. 312-317, 2016, (6 pages).
Mao, L. et al., "Enhanced bioactivity of Mg—Nd—Zn—Zr alloy achieved with nanoscale MgF2 surface for vascular stent application," ACS Appl Mater Interfaces, 2015, vol. 7, No. 9, pp. 5320-5330, abstiact, p. 5320, right column, line 2 from the bottom to p. 5321, left column, line 2, section of "Materials and surface modification", (11 Pages).
Liu et al., "Multifunctional MgF2/polydopamine coating on Mg alloy for vascular stent application," Journal of Materials Science and Technology, vol. 31, ISSN: 1005-0302, pp. 733-743, 2015, (11 pages).
Kubota, "Properties of Magnesium Alloys & Their Technology", Journal of the Surface Finishing Society of Japan, vol. 53, No. 3, pp. 8-11, 2002, with machine English translation, (7 pages).
First Chinese Office Action and English Translation thereof for Chinese Application No. 201980005605.0, dated Dec. 18, 2020 (15 pages).
English Abstract for CN101468216A.
English Abstract for CN102387825A.
English Abstract for CN104498790A.
English Abstract for CN107385419A.
English Abstract for JP2842943B2.
English Abstract for JP5425364B2.
English Abstract for JP5701497B2.
English Abstract for JP2005531391A.
English Abstract for JP2006087704A.
English Abstract for JP2009530039A.
English Abstract for JP2010503486A.
English Abstract for JP2013215332A.
English Abstract for JP2014534841A.
English Abstract for JP2017501756A.
English Abstract for WO2018122418A1.
English Abstract for WO2018139647A1.

(56) References Cited

OTHER PUBLICATIONS

Second Chinese Office Action, and English Machine Translation thereof, for corresponding Chinese Patent Application No. 201780082913.4, dated Apr. 25, 2021, (9 pages).
First Chinese Office Action, and English Machine Translation thereof, for Chinese Patent Application No. 201880009024.X, dated Apr. 6, 2021, (9 pages).
First Examination Report for Indian Patent Application No. 201917028971, dated Mar. 22, 2021, (6 pages).
Second Chinese Office Action, and English Machine Translation thereof, for Chinese Patent Application No. 201980005605.0, dated May 17, 2021, (17 pages).
Second Chinese Office Action, and English Machine Translation thereof, for Chinese Patent Application No. 201880086293.6, dated Jul. 23, 2021, (10 pages).
Extended European Search Report for European Patent Application No. 18926369.2, dated May 18, 2021, (8 pages).
E-Space English Abstract for CN101257860A.
E-Space English Abstract for CN101468216A.
E-Space English Abstract for CN102548589A.
E-Space English Abstract and machine translation for JP09256099A.
E-Space English Abstract for WO2015147184A1.
E-Space English Abstract and machine translation for CN1809701A.
E-Space English Abstract for CN102719717A.
E-Space English Abstract for CN105143483A.
E-Space English Abstract for CN105586521A.
Decision of Rejection, and English Machine Translation thereof, for Chinese Patent Application No. 201980005605.0, dated Aug. 4, 2021, (10 pages).
Decision on Rejection, and English Translation thereof, for Chinese Application No. 201780082913.4, dated Aug. 31, 2021, (12 pages).
Indian Office Action for Indian Application No. 201917027629, dated Oct. 27, 2021, (6 pages).
"Microstructure and properties", retrieved from "https://www.researchgate.net/publication/282288987_Microstructure and_ properties_of_Mg-sZn-08Zr-xMn_alloy" on Nov. 23, 2021, (4 pages).
Final Office Action, U.S. Appl. No. 17/138,492 dated Sep. 15, 2021, (18 pages).

* cited by examiner

MAGNESIUM ALLOY

CROSS REFERENCE TO THE RELAYED APPLICATION

This application is a continuation application, under 35 U.S.C. § 111(a), of international application No. PCT/JP2017/046768, filed on Dec. 26, 2017, which claims priority on Japanese Patent Application No. 2017-001887 filed on Jan. 10, 2017, the entire content of which is incorporated herein as a part of the application.

FIELD OF THE INVENTION

The present invention relates to a magnesium alloy. Specifically, the present invention relates to a magnesium alloy for medical use, having controlled biodegradability and excellent deformability.

BACKGROUND OF THE INVENTION

Conventionally, there have been developed various medical metal devices such as stents, staplers, and artificial joints. Usually, once a metal device is implanted in a living body, the metal device remains in the living body unless it is removed surgically. In some filed of application, a metal device is desired to retain its strength for a certain period of time from the beginning of its implantation, while the same device is desired to be degraded and be absorbed in the living body after the repairing of living tissue. Magnesium is a less-toxic highly biosafe metal, and is rapidly degraded and absorbed in body fluids. Therefore, various efforts have been carried out to develop magnesium and magnesium alloys used as biodegradable metal materials for medical use.

For example, WO2007/108450 describes a magnesium-based medical biodegradable material including crystallized magnesium or magnesium alloy, and magnesium oxides or magnesium hydroxides formed on the surfaces of the crystals by anodic oxidation. WO2007/108450 described that, where the magnesium-based material contains a second component other than magnesium, the second component is segregated to grain boundaries of crystals at a concentration of not less than 1.2 times of the average concentration of the second component within the crystals.

Where a magnesium alloy is used as a biodegradable medical material, the material is required to maintain its strength until the time that the living tissue of the affected part is repaired. At a state in contact with body fluid, galvanic corrosion of magnesium alloy proceeds rapidly where the magnesium alloy has contact with electrically more noble metal. Therefore, it is preferable to avoid phase separation of matrix phase of a magnesium alloy so as to avoid the rapid corrosion. Where a magnesium alloy is used as a material of a deformable medical device such as stents, the alloy preferably has appropriate deformability (ductility) and is free from coarse precipitates (compounds) which may act as starting points of fracture after the deformation.

An object of the present invention is to provide a magnesium alloy having appropriately controlled corrosion rate and excellent deformability.

SUMMARY OF THE INVENTION

A magnesium alloy according to the present invention contains, in % by mass, 1.0 to 2.0% of Zn, 0.05 to 0.80% of Zr, 0.05 to 0.40% of Mn, and the balance consisting of Mg and unavoidable impurities.

The above-described magnesium alloy has a microstructure in which fine Zr-bearing precipitates are dispersed in an alloy composed of single-phase solid solution. Since the alloy has excellent deformability (ductility, elongationability) and single matrix phase, it is possible to avoid corrosion due to the potential difference and occurrence of magnesium compounds which may act as starting points of fracture after the deformation.

The above-described magnesium alloy may further contain, in % by mass, 0.005% or more and less than 0.20% of Ca.

Preferably, in the above-described magnesium alloy, an amount of each of Fe, Ni, Co, and Cu contained as the unavoidable impurities is less than 10 ppm. In the magnesium alloy of such constitution, it is possible to further suppress the degradation rate.

Preferably, in the above-described magnesium alloy, a total content of the unavoidable impurities is 30 ppm or less, and the magnesium alloy is free from rare earth elements and aluminum.

The above-described magnesium alloy may have an average crystal grain size of 1 to 10 μm.

The magnesium alloy may have, in the values measured according to JIS Z2241, a tensile strength of 230 to 380 MPa, a proof stress of 180 to 330 MPa, and a fracture elongation (elongation after fracture) of 10 to 30%.

Preferably, the above-described magnesium alloy does not include precipitates having a grain size of 500 nm or more.

A medical device according to the present invention is a medical device that includes a metal member including the above-described magnesium alloy according to the present invention. In such a medical device, a shape of the metal member deformed in a body can be maintained stably. Therefore, it is possible to control biodegradability of the metal member appropriately.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

The present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims.

DESCRIPTION OF EMBODIMENTS

Embodiments of the present invention will be described in the following.

[Magnesium Alloy]

A magnesium alloy according to the present invention contains, in % by mass, 1.0 to 2.0% of Zn, 0.05 to 0.80% of Zr, 0.05 to 0.40% of Mn, and the balance consisting of Mg and unavoidable impurities. The magnesium alloy may further contain, in % by mass, 0.005% or more and less than 0.20% of Ca. That is, the above-described magnesium alloy may contain, in % by mass, 1.0 to 2.0% of Zn, 0.05 to 0.80% of Zr, 0.05 to 0.40% of Mn, 0.005% or more and less than 0.20% of Ca, and the balance consisting of Mg and unavoidable impurities.

Figure 1:
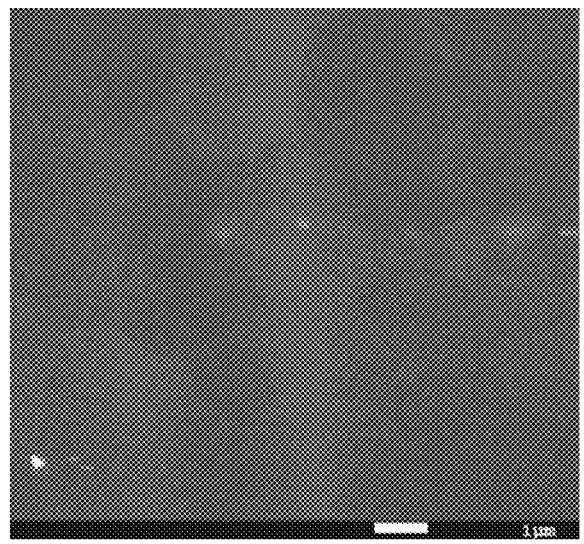
FIG. 1 is a SEM (Scanning Electron Microscope) image showing a microstructure of magnesium alloy according to Example 1 of the present invention.
Figure 2:
FIG. 2 is a SEM image showing a microstructure of magnesium alloy according to Example 6 of the present invention.
Figure 3:
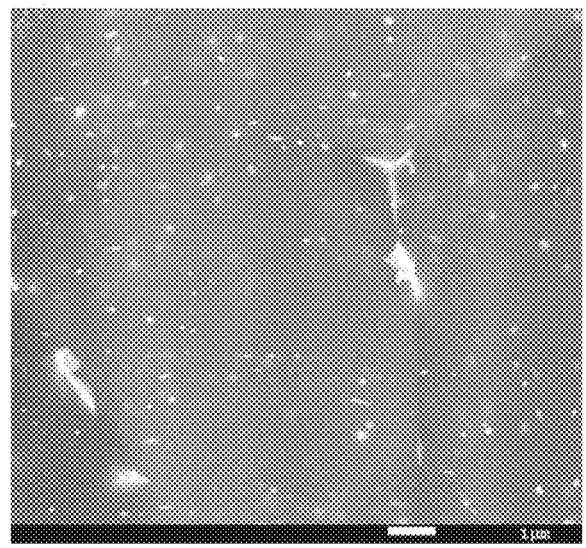
FIG. 3 is a SEM image showing a microstructure of magnesium alloy according to Comparative Example 1 of the present invention.

Magnesium alloy of the above-described composition may be made to have a complete solid-solution type alloy structure comprising a single-phase matrix. Therefore, it is possible to avoid the problem of corrosion caused by potential difference due to phase separation of magnesium alloy. Further, since generation of coarse precipitates (which may serve as a starting points of fracture) is avoided, it is possible to reduce the probability of fracture during and after the deformation. Zr is added to reduce the grain sizes of the alloy crystals and forms precipitates. However, those Zr-containing precipitates have nanometric size and are dispersed in the matrix phase, and therefore, their influence on the deformation and corrosion of alloy is almost negligible. For example, FIG. 1, FIG. 2, and FIG. 3 show SEM images of below described Example 1, Example 6, and Comparative Example 1 respectively. In each of the figures, magnesium alloy appears as the darker region with some contrast, and the white bar in the lower part of the figure is a scale of 1 μm. In FIG. 1, only small number of precipitates having grain sizes smaller than 500 nm are observed inside the crystal grains. In FIG. 2, precipitates having grain size exceeding 500 nm are observed in the crystal grain boundaries. In FIG. 3, in addition to the precipitates observed in the grain boundaries of crystals, numerous spots having different contrast are observed inside the crystal grains, indicating occurrence of compounds generated by phase separation.

Zinc (Zn): In % by Mass, 1.0% or More and 2.0% or Less

Zn is added to form a solid-solution with Mg and to enhance strength and elongation of the alloy. Where the amount of Zn is less than 1.0%, intended effect cannot be obtained. Where the amount of Zn exceeds 2.0%, Zn content exceeds the solid-solubility limit, resulting in non-desired formation of Zn-rich precipitates that reduce the corrosion resistance. Therefore, the amount of Zn is regulated to 1.0% or more and 2.0% or less. Zn content may be less than 2.0%. Preferably, Zn content is 1.4% or more and 1.7% or less.

Zirconium (Zr): In % by Mass, 0.05% or More and 0.80% or Less

Zr scarcely forms solid-solution with Mg, and forms fine-grained precipitates, thereby preventing coarsening of crystal grains of alloy. Where the amount of Zr is less than 0.05%, effects of Zr addition cannot be obtained. Where the amount of Zr exceeds 0.80%, precipitates are formed in excessive amount, thereby reducing processability of the alloy. Therefore, the amount of Zr is regulated to 0.05% or more and 0.80% or less. Preferably, Zr content is 0.2% or more and 0.6% or less.

Manganese (Mn): In % by Mass, 0.05% or More and 0.40% or Less

Mn has effects of refining grain size of alloy and enhancing corrosion resistance of alloy. Where the amount of Mn is less than 0.05%, intended effect cannot be obtained. Where the amount of Mn exceeds 0.40%, workability in plastic working is degraded. Therefore, the amount of Mn is regulated to 0.05% or more and 0.40% or less. Preferable content of Mn is 0.2% or more and 0.4% or less.

Calcium (Ca): Where Necessary, in % by Mass, 0.05% or More and Less than 0.20%

Optionally, Ca may be added into the magnesium alloy, since the addition of Ca allows one to expect enhancement of corrosion resistance while maintaining strength of magnesium alloy. Where the amount of Ca is less than 0.005%, the addition of Ca provides no effects. Where 0.20% or more of Ca is added, precipitates tend to be formed, making it impossible to obtain complete solid-solution of single phase. Therefore, where Ca is added, the amount of Ca is regulated to be 0.005% or more and less than 0.20%. Preferable amount of Ca is 0.05% or more and less than 0.10%.

[Unavoidable Impurities]

It is preferred to control the amount of unavoidable impurities where the magnesium alloy is used as a medical material. Since Fe, Ni, Co, and Cu enhance corrosion of magnesium alloy, it is preferable to control an amount each of these elements to be less than 10 ppm respectively, more preferably 5 ppm or less. Preferably, the magnesium alloy is substantially free from these elements. Preferably, total amount of unavoidable impurities is controlled to be 30 ppm or less, more preferably 10 ppm or less. Preferably, the magnesium alloy is substantially free from rare earth elements and aluminum. Where an amount of an impurity element in the alloy is less than 1 ppm, it is regarded that the alloy is substantially free from the impurity element. The amount of unavoidable impurities may be determined, for example, by ICP emission spectrometry.

[Production of Magnesium Alloy]

The above-described magnesium alloy can be produced, in accordance with usual production method of magnesium alloys, throwing ground metals or alloys of Mg, Zn, Zr, and Mn, and where necessary, Ca into a crucible, melting the ground metals and/or alloys in the crucible at a temperature of 650 to 800° C. to form a molten alloy, and casting the molten alloy. Where necessary, the cast alloy is subjected to solution heat treatment. Rare earth element-free (and aluminum-free) metals are used as the ground metals. It is possible to suppress the amounts of Fe, Ni, and Cu in the impurities by the use of ground metals with high purity. Fe, Ni, and Co in the impurities of molten alloy may be removed by iron-extraction treatment. In addition, or alternatively, it is possible to use ground metals produced by distillation refining.

[Metal Microstructure and Mechanical Properties of Alloy]

By the above-described controls of composition and production process, it is possible to obtain magnesium alloy having an average crystal grain size of 1 to 10 Fine precipitates containing Zr may be controlled to have a grain size smaller than 500 nm. Preferably, the matrix phase except for the Zr precipitates is a complete solid-solution of Mg—Zn—Mn ternary alloy or a complete solid-solution of Mg—Zn—Mn—Ca quaternary alloy.

As mechanical properties measured in accordance with JIS Z2241, the alloy has a tensile strength of 230 to 380 MPa, a proof stress of 180 to 330 MPa, and a fracture elongation of 10 to 30%. In the corrosion experiment performed to obtain an index of biodegradability, the degradation rate of the alloy is kept to be smaller than that of pure magnesium.

[Medical Device]

The magnesium alloy according to the present invention has excellent ductility and biodegradability with a degradation speed that is controlled to be lower than that of pure magnesium. In addition, the magnesium alloy is controlled to have components and their concentrations that do not cause biotoxicity. Therefore, the magnesium alloy has excellent properties as a metal for medical use. The magnesium alloy of the present invention can be appropriately used as metal members that constitute medical devices such as stents, staplers, screws, plates, coils, or the like.

Examples

[Preparation of Magnesium Alloy]

Calcium and high purity ground metals of Mg, Zn, Mn, and Zr were prepared as raw materials. Respective components were weighted so as to constitutes the component concentration shown in Table 1, and were thrown into a crucible, and were molten at 730° C. Each melt was stirred in the crucible, and was cast to form an ingot. The thus-obtained magnesium alloys of Examples 1 to 7 were made to have a blending ratio within the range of the present invention, and a magnesium alloy of Comparative Example 1 was made to have a blending ratio outside the range of the present invention. Rare earth elements and aluminum were not contained in the raw materials even as unavoidable impurities. In Examples 1 to 6 and Comparative Example 1, magnesium was provided from a magnesium ground metal of purity level of 99.99% with low concentration of impurity Cu, and molten alloys in the crucible were subjected to iron-extraction treatment so as to remove iron and nickel from the molten alloys. Example 7 was prepared to have relatively high impurity concentration by selection of raw materials, and omitting the iron-extraction treatment. Impurity concentrations of the thus obtained samples were measured using an ICP emission spectrometer (AGILENT 720 ICP-OES made by Agilent Technologies). The components of Examples and Comparative Example are shown in Table 1. In each of Examples 1 to 6 and Comparative Example 1, total amount of impurities was not more than 30 ppm, and respective concentrations of Fe, Ni, and Cu were each not more than 9 ppm, and Al and rare earth elements were not detected. In Example 7, total amount of impurities exceeded 30 ppm, and respective concentrations of Fe, Ni, and Cu were each 10 ppm or more. Concentrations of components and concentrations of impurity Fe, Ni, Co, Cu of the Examples and Comparative Example are shown in Table 1. ND in the Table denotes that that the amount was under detection limit.

TABLE 1

| | Component concentration (% by mass) | | | | | Impurity concentration (ppm) | | | |
|---|---|---|---|---|---|---|---|---|---|
| | Mg | Zn | Mn | Zr | Ca | Fe | Ni | Co | Cu |
| Example 1 | Balance | 1.5 | 0.3 | 0.5 | 0.05 | 8 | 8 | ND | 1 |
| Example 2 | Balance | 1.0 | 0.3 | 0.5 | 0 | 6 | 8 | ND | 1 |
| Example 3 | Balance | 1.9 | 0.3 | 0.5 | 0 | 9 | 9 | ND | 1 |
| Example 4 | Balance | 1.5 | 0.3 | 0.5 | 0 | 5 | 5 | ND | 1 |
| Example 5 | Balance | 0.9 | 0.3 | 0.5 | 0.05 | 7 | 8 | ND | 1 |
| Example 6 | Balance | 1.5 | 0.3 | 0.5 | 0.10 | 8 | 6 | ND | 1 |
| Example 7 | Balance | 1.5 | 0.3 | 0.5 | 0.05 | 18 | 12 | ND | 23 |
| Comparative Example 1 | Balance | 2.1 | 0.3 | 0.5 | 0.05 | 8 | 7 | ND | 2 |

[Measurement of Mechanical Properties]

The alloys of the Examples and Comparative Example were respectively worked to round rods by heat extrusion, and each rod was subjected to measurements of tensile strength, proof stress, and fracture elongation according to JIS Z2241. The results are shown in Table 2.

[Observation of Metal Microstructure]

A sectional plane of each extruded rod was made to have a clean surface by Ar ion beam sputtering. The cleaned surface was observed using a scanning electron microscope (JEOL SDM-7000F), and average grain size was measured using electron backscatter diffraction (EBSD) method. The results are shown in Table 2. Occurrence of precipitates was also observed in the observation area of 2 mm×2 mm in each sample. Where precipitates having a grain size of 500 nm or more were not observed in the observation area of a sample, the sample was evaluated as A. Where precipitates having a grain size of 500 nm or more were observed in the observation area of a sample, the sample was evaluated as B. Where the matrix phase showed phase separation into two or more phases, the sample was evaluated as C. The results are shown in Table 2.

[Measurement of Degradability]

A disk-shaped sample of 10 mm in diameter and 1 mm in thickness was obtained from each alloy. After mirror-polishing both faces, each sample was dipped in physiological saline solution at 37° C. After removing corrosion product, degradability of the sample (as an indicator of biodegradability) was evaluated based the weight loss of the sample after the experiment compared to the weight of the sample before the experiment. The results are shown in Table 2.

TABLE 2

| | Strength (MPa) | Proof stress (MPa) | Elongation (%) | Average grain size (μm) | Degradability (mm/y) | Result of microstructure observation |
|---|---|---|---|---|---|---|
| Example 1 | 250 | 195 | 15 | 7 | 1.37 | A |
| Example 2 | 230 | 180 | 20 | 9 | 1.42 | A |
| Example 3 | 260 | 210 | 16 | 6 | 1.63 | A |
| Example 4 | 260 | 195 | 15 | 6 | 1.55 | A |
| Example 5 | 230 | 180 | 19 | 10 | 1.68 | A |
| Example 6 | 250 | 195 | 15 | 7 | 2.71 | B |
| Example 7 | 250 | 195 | 15 | 7 | 3.20 | A |
| Comparative 1 | 280 | 230 | 13 | 6 | 3.34 | C |

From the results of measurement of degradability, it is understood that compared to Examples 1 to 7 having main component concentrations within the range of the present invention, corrosion by the physiological saline solution proceeded rapidly in Comparative Example having main component concentration outside the range of the present invention and occurring phase separation. Precipitates having a grain size of 500 nm or more are formed in Example 6, and the presence of those precipitates may participate in relatively high corrosion speed. In such a case, heat treatment is required to reduce the precipitates. In Example 7, even though the result of observation of microstructure is satisfactory, each concentration of Fe, Ni, and Cu contained as impurities exceeded 10 ppm, resulting in degradation speed close to that of Comparative Example.

The magnesium alloy provided by the present invention is excellent in deformability. The magnesium alloy has complete solid solution type single phase matrix, and thereby avoiding corrosion due to potential difference. Therefore, it is possible to control degradation speed in the living body appropriately. Therefore, the magnesium alloy has high applicability as metal members of medical device such as stents and staplers that are deformed in practical use and are required to have stable biodegradability.

What is claimed is:

1. A magnesium alloy consisting of, in % by mass, 1.0 to 2.0% of Zn, 0.05 to 0.80% of Zr, 0.05 to 0.40% of Mn, and the balance consisting of Mg and unavoidable impurities, wherein the magnesium alloy consists of a matrix phase composed of single-phase solid solution and Zr-bearing precipitates dispersed in the matrix phase, wherein an amount of each of Fe, Ni, Co, and Cu as unavoidable impurities is less than 10 ppm, a total content of the unavoidable impurities is 30 ppm or less, and grain sizes of the precipitates are smaller than 500 nm.

2. A magnesium alloy consisting of, in % by mass, 1.0 to 2.0% of Zn, 0.05 to 0.80% of Zr, 0.05 to 0.40% of Mn, 0.005% to less than 0.20% of Ca, and the balance consisting of Mg and unavoidable impurities, wherein the magnesium alloy consists of matrix phase composed of single-phase solid solution and Zr-bearing precipitates dispersed in the matrix phase, wherein an amount of each of Fe, Ni, Co, and Cu as unavoidable impurities is less than 10 ppm, a total content of the unavoidable impurities is 30 ppm or less, and grain sizes of the precipitates are smaller than 500 nm.

3. The magnesium alloy according to claim 1, wherein the magnesium alloy is free from rare earth elements and aluminum.

4. The magnesium alloy according to claim 1, wherein an average grain size of the matrix phase is 1 to 10 μm.

5. The magnesium alloy according to claim 1, having, in the values measured according to JIS Z2241, a tensile strength of 230 to 380 MPa, a proof stress of 180 to 330 MPa, a fracture elongation of 10 to 30%.

6. A medical device including a metal member comprising the magnesium alloy according to claim 1.

7. The magnesium alloy according to claim 2, wherein the magnesium alloy is free from rare earth elements and aluminum.

8. The magnesium alloy according to claim 2, wherein an average grain size of the matrix phase is 1 to 10 μm.

9. The magnesium alloy according to claim 2, having, in the values measured according to JIS Z2241, a tensile strength of 230 to 380 MPa, a proof stress of 180 to 330 MPa, a fracture elongation of 10 to 30%.

10. A medical device including a metal member comprising the magnesium alloy according to claim 2.

* * * * *